United States Patent [19]
Sims et al.

[11] Patent Number: 5,955,441
[45] Date of Patent: Sep. 21, 1999

[54] GENETIC INHIBITION OF COMPLEMENT MEDIATED INFLAMMATORY RESPONSE

[75] Inventors: Peter J. Sims, Oklahoma City, Okla.; Alfred L.M. Bothwell, Guilford, Conn.

[73] Assignees: Oklahoma Medical Research Foundation, Oklahoma City, Okla.; Yale University, New Haven, Conn.

[21] Appl. No.: 08/696,777

[22] Filed: Aug. 13, 1996

Related U.S. Application Data

[62] Division of application No. 08/271,562, Jul. 7, 1994, Pat. No. 5,573,940, which is a continuation of application No. 07/729,926, Jul. 15, 1991, abandoned, which is a continuation-in-part of application No. 07/365,199, Jun. 12, 1989, Pat. No. 5,135,916.

[51] Int. Cl.⁶ .................................................. A01N 43/04
[52] U.S. Cl. ................................................................. 514/44
[58] Field of Search ........................ 514/44, 2; 424/93.1, 424/93.21; 435/172.3; 530/350

[56] References Cited

PUBLICATIONS

Walsh et al. Transfection of human CD59 complementary DNA into rat cells confers resistance to human complement. Eur. J. of Immun., vol. 21, No. 3, pp. 847–850, Mar. 1991.

Weatherall, D J. Scope and limitations of gene therapy. British Medical Bulletin, vol. 51, No. 1, pp. 1–11, 1995.

NIH panel. Report and recommendations of the Panel to Assess the NIH investment in research on gene therapy, Dec. 07, 1995.

*Primary Examiner*—Brian R. Stanton
*Assistant Examiner*—Deborah J. R. Clark
*Attorney, Agent, or Firm*—Arnall Golden & Gregory, LLP

[57] ABSTRACT

A method and means for protecting cells and transplanted organs from the effects of activated complement proteins generated in blood serum or plasma by introducing the gene for CD59 into the cells to be protected is described. In an example of the method, protection against the pore-forming activity of the human C5b-9 proteins was conferred on CHO cells by transfection with cDNA encoding the human complement regulatory protein CD59.

15 Claims, 3 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 103 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

```
Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
                20                  25                  30

Leu Gln Val Tyr Asn Lys Cys Trp Lys Phe Glu His Cys Asn Phe Asn
            35                  40                  45

Asp Val Thr Thr Arg Leu Arg Glu Asn Glu Leu Thr Tyr Tyr Cys Cys
        50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Leu Val Thr Pro Phe Leu Ala
                85                  90                  95

Ala Ala Trp Ser Leu His Pro
            100
```

(2) INFORMATION FOR SEQ ID NO:2:

(i) SEQUENCE CHARACTERISTICS:
       (A) LENGTH: 315 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

CTGCAGTGCT ACAACTGTCC TAACCCAACT GCTGACTGCA AAACAGCCGT CAATTGTTCA        60

-continued

```
TCTGATTTTG ATGCGTGTCT CATTACCAAA GCTGGGTTAC AAGTGTATAA CAAGTGTTGG         120

AAGTTTGAGC ATTGCAATTT CAACGACGTC ACAACCCGCT TGAGGGAAAA TGAGCTAACG         180

TACTACTGCT GCAAGAAGGA CCTGTGTAAC TTTAACGAAC AGCTTGAAAA TGGTGGGACA         240

TCCTTATCAG AGAAAACAGT TCTTCTGCTG GTGACTCCAT TTCTGGCAGC AGCCTGGAGC         300

CTTCATCCCT AAGTC                                                         315
```

GENETIC INHIBITION OF COMPLEMENT MEDIATED INFLAMMATORY RESPONSE

This application is a Divisional of Ser. No. 08/271,562, filed Jul. 7, 1994, U.S. Pat. No. 5,573,940, by Peter J. Sims and Alfred L. M. Bothwell for *"Genetic Inhibition of Complement Mediated Inflammatory Response,"* which is a continuation of Ser. No. 07/729,926, filed on Jul. 15, 1991, now abandoned which is a continuation-in-part of Ser. No. 07/365,199, filed Jun. 12, 1989, U.S. Pat. No. 5,135,916.

The United States government has rights in this invention by virtue of National Institutes of Health grant numbers HL36061 and GM40924.

BACKGROUND OF THE INVENTION

The present invention generally relates to compositions, and methods for use thereof, effective in regulating inflammatory platelet and endothelial stimulatory and coagulopathic responses by modulating the activity of the C5b-9 complex of the human plasma complement system by genetic manipulation.

The complement system is a complex interaction of plasma proteins and membrane cofactors which act in a multi-step, multi-protein cascade sequence in conjunction with other immunological systems of the body to provide immunity from intrusion of foreign cells. Complement proteins represent up to about 10% of globulins in normal serum of man and other vertebrates.

The classic complement pathway involves an initial antibody recognition of, and binding to, an antigenic site (SA) on a target cell. This surface bound antibody subsequently reacts with the first component of complement, C1q, forming a C1-antibody complex with Ca++, C1r, and C1s which is proteolytically active. C1s cleaves C2 and C4 into active components, C2a and C4a. The C4b,2a complex is an active protease called C3 convertase, and acts to cleave C3 into C3a and C3b. C3b forms a complex with C4b,2a to produce C4b,2a,3b, which cleaves C5 into C5a and C5b. C5b combines with C6. The C5b,6 complex combines with C7 to form the ternary complex C5b,6,7. The C5b,6, 7 complex binds C8 at the surface of the cell, which may develop functional membrane lesions and undergo slow lysis. Upon binding of C9 to the C8 molecules in the C5b,6,7,8 complex, lysis of bacteria and other foreign cells is rapidly accelerated.

Recently, the C5b-9 proteins of the human plasma complement system have been implicated in non-lytic stimulatory responses from certain human vascular and blood cells. The capacity of C5b-9 to modify membrane permeability and to selectively alter ion conductance is thought to elicit these non-lytic responses from human cells. In the case of human blood platelets and vascular endothelium, assembly of the C5b-9 complex initiates a transient and reversible depolarization of the plasma membrane potential, a rise in cytosolic Ca2+, metabolic conversion of arachidonate to thromboxane or prostacyclin, and the activation of intracellular protein kinases. In addition, human platelets exposed to C5b-9 undergo shape changes, secretory fusion of intracellular storage granules with plasma membrane, and the vesiculation of membrane components from the cell surface. Human endothelial cells exposed to the human C5b-9 proteins secrete high molecular weight multimers of the platelet adhesion protein, von Willibrand Factor (vWF), and the intracellular granule membrane protein, GMP140, is translocated from the Weible-Palade body to the endothelial surface. High molecular weight multimers of vWF have been implicated in the pathogenesis of vaso-occlusive platelet adherence to endothelium and cell surface GMP140 has been implicated in the adherence of inflammatory leukocytes to endothelium.

These effects of complement proteins C5b-9 on platelet and endothelial cells alter the normal regulation of the enzymes of the plasma coagulation system at these cell surfaces. For example, the generation of platelet membrane microparticles by vesiculation results in the exposure of membrane binding sites for coagulation factor Va. Binding of factor Va to these membrane microparticle sites initiates assembly of the prothrombinase enzyme complex. This complex in turn accelerates coagulation factor Xa activation of prothrombin to thrombin which promotes plasma clotting. Similarly, C5b-9 binding to the endothelial cell results in the exposure of plasma membrane receptors for the prothrombinase complex, thereby accelerating the generation of thrombin from prothrombin at the endothelial surface.

This interaction between components of the complement and coagulation systems at the surface of blood platelets and endothelium can generate inflammatory and chemotactic peptides at sites of vascular thrombus formation and may contribute to the altered hemostasis associated with immune disease states. In addition, immune reactions affecting blood platelets and endothelium can lead to platelet aggregation, the secretion of proteolytic enzymes and vasoactive amines from platelet storage granules, and increase adherence of platelets and leukocytes to the endothelial lining of blood vessels.

It has been demonstrated that membrane-uptake of C3b and C5b-9 proteins can occur spontaneously during incubation of platelets in citrated plasma. Complement activation can also occur during blood collection as a result of exposure to plastic surfaces supporting the C3-convertase reaction. While the implications of complement activation during blood collection and in vitro storage for transfusion have not been directly addressed it is, nevertheless, known that plasma levels of coagulation factors V and VIII rapidly decline in stored platelet concentrates at a rate considerably faster than their decay in cell-free plasma, suggesting consumptive loss. Further, platelet collection and storage is associated with an increase in vesicular plasma membrane microparticles, a product of C5b-9 initiated platelet secretion. These physiological and enzymatic changes greatly reduce the potential shelf life of stored platelets, particularly platelet-rich plasma concentrates used for transfusions, which is generally only 72 hours at best. Furthermore, this interaction of activated C5b-9, platelets, and coagulation factors in stored platelet concentrates will adversely affect the hemostatic effectiveness of these units when infused.

In vitro human organ and tissue storage and survival of the transplanted graft is also adversely affected by the spontaneous activation of the complement system, resulting in membrane insertion of the C5b-9 proteins into vascular endothelium. Activation of C5 to C5a and C5b has been shown to be catalyzed by plastics and other synthetic membranes required to maintain perfusion of vascular beds during in vitro tissue and organ storage. In addition, membrane deposition of C5b-9 in vivo has been implicated in the acute rejection of transplanted tissue due to immune activation of the recipient's plasma complement system against the endothelial cells within the donor's organ.

Assembly of the C5b-9 complex is normally limited in plasma by the amount of C5b generated by proteolysis of C5 to its biologically-active fragments C5b and C5a. In addition to plasmin and other plasma or cell-derived proteases, two enzymes of the complement system can cleave C5 to C5a and C5b, the membrane-stabilized enzyme complexes C4b2a and C3bBb (C5- convertases). The activity of these two enzymes is normally inhibited on the surface of human blood and vascular membranes by the plasma membrane proteins, "membrane cofactor protein" (CD46), described by Lublin and Atkinson, *Current Topics Microbiol. Immunol.* 153:123 (1989) and "decay-accelerating factor" (CD55), Medof, et al., *J. Exp. Med.* 160:1558 (1984).

Platelet and endothelial cell activation by C5b-9 also has ramifications in autoimmune disorders and other disease states. The importance of spontaneous complement activation and the resulting exposure of platelets and endothelium to activated C5b-9 to the evolution of vaso-occlusive disease is underscored by consideration that a) leukocyte infiltration of the subendothelium, which is known to occur in regions of atheromatous degeneration and suggests localized generation of C5a at the vessel wall, is potentially catalyzed by adherent platelets and b) local intravascular complement activation resulting in membrane deposition of C5b-9 complexes accompanies coronary vessel occlusion and may affect the ultimate extent of myocardial damage associated with infarction.

There is now considerable evidence that the human erythrocyte membrane as well as the plasma membranes of other human blood cells and vascular endothelium are normally protected from these effects of complement by cell-surface proteins that specifically inhibit activation of the C5b-9 pore upon C9 binding to membrane C5b-8, as reported by Holguin, M. H., et al., *J. Clin. Invest.* 84, 7–17 (1989); Sims, P. J., et al., *J. Biol. Chem.* 264, 19228–19235 (1989); Davies, A., et al., *J. Exp. Med.* 170, 637–654 (1989); Roilins, S. A., and Sims, P. J. *J. Immunol.* 144, 3478–3483 (1990); and Hamilton, K. K., et al., *Blood* 76, 2572–2577 (1990). Plasma membrane constituents reported to exhibit this activity include homologous restriction factor (HRF) (C8-binding protein), with an apparent molecular mass of 65 kDa, as described by Zalman, L. S., et al., *Proc. Natl. Acad. Sci., U.S.A.* 83, 6975–6979 (1986) and Schonermark, S., et al., *J. Immunol.* 136, 1772–1776 (1986), and the leukocyte antigen CD59, a glycoprotein with an apparent molecular mass of 18–21 kDa, described by Sugita, Y., et al., *J. Biochem.* (Tokyo) 104, 633–637 (1988); Holguin, M. H., et al., (1989); Sims, P. J., et al., (1989); Davies, A., (1989); Rollins, S. A., and Sims, P. J. (1990); and Hamilton, K. K., et al., (1990). Accumulated evidence suggest that these two proteins exhibit quite similar properties, including the following: (1) both HRF and CD59 are tethered to the cell surface by a glycolipid anchor, and are deleted from the membranes of the most hemolytically sensitive erythrocytes that arise in the stem cell disorder paroxysmal nocturnal hemoglobinuria; (2) the activity of both inhibitors is species-restricted, showing selectivity for C8 and C9 that are derived from homologous (i.e. human) serum; and (3) both HRF and CD59 appear to function by inhibiting the activation of C9, decreasing the incorporation of C9 into the membrane C5b-9 complex, and limiting propagation of the C9 homopolymer.

In U.S. Pat. No. 5,135,916, Sims and Wiedmer disclose compositions and methods for use thereof relating to polypeptides having the ability to act as an inhibitor of complement C5b-9 complex activity. The compositions contain CD59, an 18 kDa protein found on the surface of human erythrocytes, active derivatives or fragments thereof which act to inhibit the activity of C5b-9, anti-idiotypic antibodies mimicking the action of the inhibitor proteins or antibodies against C7 or C9 which block the formation of the C5b-9 complex. The compositions can be used in vitro to inhibit C5b-9 related stimulatory responses of platelets and vascular endothelium of perfused organs and tissues, thereby preventing the C5b-9 initiated cell necrosis or stimulated secretion of proteolytic enzymes and the exposure of the procoagulant membrane receptors during collection and in vitro storage. In one variation of this embodiment, the vascular endothelium of organs and tissues to be transplanted are treated with these compositions to protect these cells from complement activation after transplantation. In another embodiment, immune disease states are treated by administering an effective amount of a C5b-9 inhibitor to suppress C5b-9 mediated platelet activation in vivo. Also disclosed are methods for the production of isolated polypeptides that are able to suppress complement C5b-9 mediated platelet and endothelial cell activation.

In the disease paroxysmal nocturnal hemoglobinuria, the red cell that is most sensitive to complement-mediated cytolysis is normally deficient in both CD55 (decay accelerating factor, the membrane inhibitor of the C3/C5-convertase) and in CD59 (the inhibitor of C5b-9). Although CD46, CD55, and CD59, serve as inhibitors of complement activation, there is now considerable evidence that CD59 provides the most effective protection from the cytolytic and cell-stimulatory effects of complement by specificcally inhibiting the activation of C9 into a membrane pore-forming structure. The deletion of CD59 from the plasma membrane renders erythrocytes highly susceptible to lysis by human plasma, an effect that is not observed when only CD55 (decay-accelerating factor) is deficient. Furthermore, an isolated deficiency of decay-accelerating factor (CD55) does not result in hemolytic disease, as reported by Lin, et al., Transfusion 28:427–429 (1988) and Telen, et al., *J. Exp. Med.* 167:1993–1998 (1988). By contrast, all of the clinical manifestation of severe paroxysmal nocturnal hemoglobinuria, including intravascular hemolysis and cerebral infarction, were observed in a patient that exhibited an isolated defect in CD59 expression (due to a mutation in the CD59 gene) with normal expression of decay-accelerating factor (CD55), as reported by Yamashina, et al., *N. E. J. Med.* 323:1184–1189 (1990).

Subsequent to U.S. Ser. No. 07/365,199, a cDNA encoding CD59 was reported by Sawada, et al., *Nucleic Acids Res.* 17(16), 6728 (submitted Jul. 25, 1989). cDNA encoding CD59 has also been cloned from human T-cell leukemia (YT) and human erythroleukemia (K562) cell lines, and CD59 antigen transiently expressed in COS cells, as reported by Philbrick, W. M., et al., *Eur. J. Immunol.* 20, 87–92 (1990). Walsh, et al., *Eur. J. Immunol.* 21:847–850 (1991), demonstrated expression of CD59 antigen with complement-inhibitory activity in rat cells transfected with cDNA for CD59.

It is an object of the present invention to provide a means and method for the modulation and inhibition of complement C5b-9 mediated platelet and endothelial cell activation in vivo and in vitro by genetic modification of cells to be transplanted or infused.

It is a further object of the present invention to provide a means and method for increasing the survival and therapeutic efficacy of platelets and tissues or organs collected and stored in vitro by genetic manipulation of the cells.

SUMMARY OF THE INVENTION

A method and means for protecting transfused cells and transplanted organs from the effects of activated complement proteins generated in blood serum or plasma by expressing in the cells the gene for CD59 and/or administering with the cells the product of expression of the gene. In the preferred embodiment, the gene for CD59, ligated to a vector suitable for high level expression of the gene in the target cells, is introduced into the cells to be protected. The gene can also be introduced into and expressed in a non-human or procaryote system such as *E. coli* for the large scale production of the protein. For example, the recombinant gene is introduced into cells to be transfused or tissue to be transplanted by transfection or infection with a vector containing the gene at 12 to 24 hours prior to infusion or transplantation. In the case of vascularized organs to be transplanted, transfection of the recombinant gene of the vascular endothelial cells lining the blood vessels is performed.

This is exemplified by the amplified gene expression in CD59-transfected CHO (Chinese Hamster Ovary) cells, which conferred protection on the cells from attack by complement. CD59 was stably expressed in Chinese hamster ovary cells using the pFRSV mammalian expression vector. After cloning and selection, the transfected cells were maintained in media containing various concentrations of methotrexate, which induced surface expression of up to $4.2 \times 10^6$ molecules of CD59/cell. Phosphatidylinositol-specific phospholipase C removed greater than 95% of surface-expressed CD59 antigen, confirming that recombinant CD59 was tethered to the Chinese hamster ovary plasma membrane by a lipid anchor. The recombinant protein exhibited an apparent molecular mass of 21–24 kDa (versus 18–21 kDa for human erythrocyte CD59). After N-glycanase digestion, recombinant and erythrocyte CD59 comigrated with apparent molecular masses of 12–14 kDa, suggesting altered structure of asparagine-linked carbohydrate in recombinant versus erythrocyte CD59. The function of the recombinant protein was evaluated by changes in the sensitivity of the CD59 transfectants to the pore-forming activity of human C5b-9. Induction of cell-surface expression of CD59 antigen inhibited C5b-9 pore formation in a dose-dependent fashion. CD59 transfectants expressing greater than or equal to $1.3 \times 10^6$ molecules of CD59/cell were completely resistant to human serum complement. By contrast, CD59 transfectants remained sensitive to the pore-forming activity of guinea pig C8 and C9 (bound to human C5b-67). Functionally blocking antibody against erythrocyte CD59 abolished the human complement resistance observed for the CD59-transfected Chinese hamster ovary cells. These results confirm that the C5b-9 inhibitory function of the human erythrocyte membrane is provided by CD59 and that the gene for this protein can be expressed in xenotypic cells to confer protection against human serum complement.

DETAILED DESCRIPTION OF THE INVENTION

Figure 1:
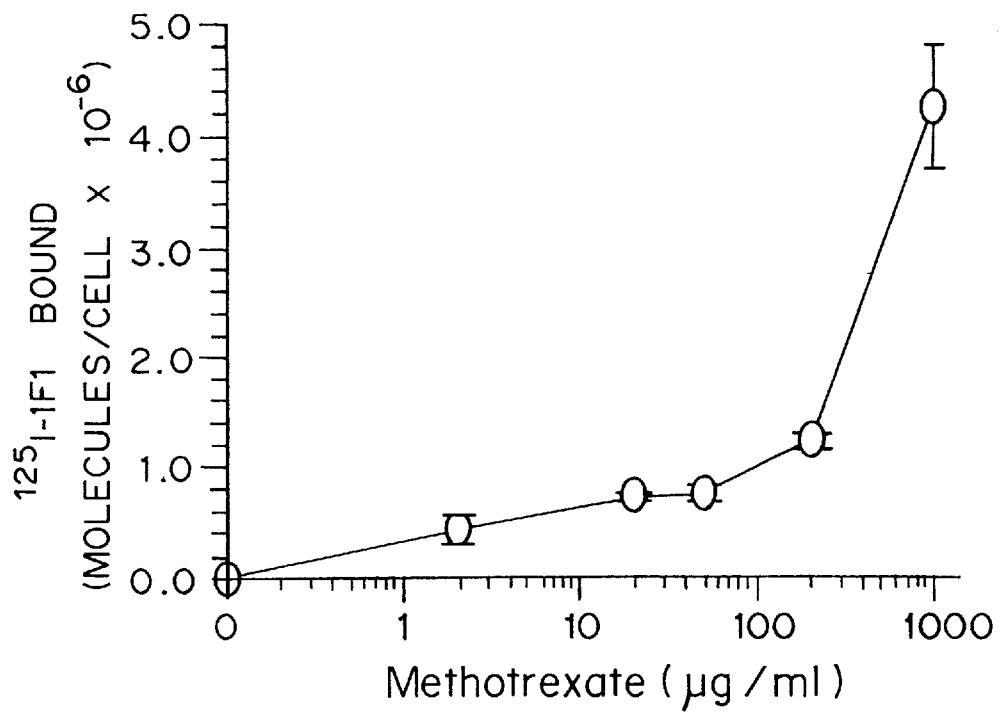
FIG. 1 is a graph of the induction of CD59 antigen in CHO cells transfected with plasmid containing human CD59 cDNA, $^{125}$I-1F1 bound CD59 (molecules/cell$\times 10^{-6}$) versus methotrexate (μg/ml). Chinese hamster ovary cells were transfected with a plasmid containing the pFRSV vector and cDNA for human CD59. After subcloning and selection, the cells were maintained in medium containing methotrexate and surface antigen measured by the specific binding of monoclonal antibody $^{125}$I-1F1 (10 μg/ml) against CD59. All data were corrected for nonspecific binding measured for control (nontransfected) CHO cells grown in the absence of methotrexate (origin). Data denote means ±S.E. of three measurements made on separate days.

The capacity to stably express CD59 in Chinese hamster ovary (CHO) cells has enabled direct evaluation of the C5b-9 inhibitory activity conferred when CD59 is selectively expressed in mammalian cells that normally express neither CD59 nor HRF. The results demonstrate that the inhibitory activity of human blood cells toward the membrane attack complex of human serum complement can be transferred to a non-human mammalian cell by transfection with the CD59 cDNA and demonstrate that the C5b-9 inhibitory function of this protein correlates with the amount of newly expressed surface CD59 antigen.

The existence of these proteins and the studies detailed below indicate that a deletion or inactivation of these cell surface components increases the risk of vascular thrombosis and leads to a decreased storage time for platelets and platelet rich plasma (PRP), and perfused organs and transplanted tissue. Accordingly, the survival and hemostatic efficacy of platelets, the survival and function of hematopoietic progenitor cells, such as CFU-S, CFU-GEMM, and CFU-L, and their progeny, such as BFU-E, BFU-MK, and CFU-GM, as well as the mature blood cells, including erythrocytes, platelets, monocytes, granulocytes, and lymphocytes, that may derive from these progenitor cells after bone marrow transplantation, as well as the survival of organs and tissue for transplant, which are collected and stored in vitro, can be increased by addition of the C5b-9 inhibitor to the storage buffer or perfusate and/or by the introduction and expression of the gene encoding CD59 in the cells to be protected. Autoimmune disorders and other disease states that involve C5b-9 mediated platelet activation, including lupus, rheumatoid arthritis, and additional types of immuno-vasculitis, can also be treated by the intravascular administration and/or transfection and expression of an effective amount of the inhibitor or a functionally active polypeptide thereof to suppress C5b-9 activity in a patient requiring such treatment. Similar uses of the inhibitor can be applicable for cell culture in human blood derived culture media.

The data provided herein are evidence that transfection with the gene for CD59 can be used to confer protection against the membrane attack complex of complement to cells that do not normally restrict activation of the human C5b-9 proteins. These data confirm by DNA transfection the C5b-9 inhibitory function that has previously been attributed to CD59 antigen present on human erythrocytes and exclude the possibility that the activity found associated with this protein reflects the presence of another membrane constituent with complement inhibitory activity that copurifies with CD59 antigen. Despite apparent differences in glycosylation, the C5b-9 inhibitory function observed for recombinant CD59 expressed in CHO cells exhibits specificity for human C8 and C9 (within C5b-9), analogous to that observed for the human erythrocyte membrane and for purified erythrocyte CD59 antigen. This capacity to confer species-selective protection against the human C5b-9 proteins by transfection of a non-human cell with cDNA encoding the CD59 sequence establishes unequivocally that this 18–21 kD protein functions as a homologous complement restriction factor on human blood cells and is consistent with the observation that the syndrome of paroxysmal nocturnal hemoglobinuria can be associated with an isolated deficiency of erythrocyte CD59.

As illustrated by the following examples, the complement inhibitory activity of recombinant CD59 was found to saturate when the expression of surface antigen was amplified to greater than or equal to $1.3 \times 10^6$ molecules/CHO cell. Assuming a spherical diameter of approximately 25 $\mu$m for the CHO cell, this is equivalent to greater than or equal to 600 molecules of CD59 antigen/$\mu$m$^2$ of plasma membrane surface. By comparison, human erythrocytes, which are highly resistant to activation and lysis by human complement, express approximately $2.5 \times 10^4$ molecules of CD59 antigen/cell, which is equivalent to approximately 200 molecules/$\mu$m$^2$ of membrane surface. Extrapolating from this data, $1 \times 10^3$ molecules CD59/cell or greater than or equal to 1 molecule of CD59 antigen/$\mu$m$^2$ of plasma membrane surface should be effective in inhibiting complement mediated activation and lysis.

The data also demonstrate that recombinant CD59 expressed in CHO cells exhibits the species-selective recognition of human C5b-9 characteristic of CD59 in human erythrocytes despite apparent differences in N-linked glycosylation. These data indicate that the species selectivity exhibited by CD59, which includes recognition for human C8 (within C5b-8) and human C9 (within C5b-9), is conferred by the core protein, independent of its carbohydrate, or that the relevant carbohydrate structures are conserved in the recombinant protein when expressed in CHO cells.

Summary of Mechanism by which CD59 inhibits the Csb-9 Inflammatory Response

As described in U.S. Ser. No. 07/365,199 filed Jun. 12, 1989, the conclusions as to the mechanisms by which the platelet bound inhibitor inhibits the C5b-9 inflammatory response were based on the following. Addition of purified CD59, isolated from human erythrocyte membranes, to other blood cells or endothelium served to protect these cells from both the cytolytic and cell-stimulatory effects of the C5b-9 complement proteins. The function of CD59, when bound to platelet and endothelial cell surfaces, was also probed by raising a neutralizing (blocking) antibody ($\alpha$-P18) that abrogates the C5b-9 inhibitory function of the purified molecule in vitro as well as the endogenous C5b-9 inhibitory factors, which includes CD59. When bound to the platelet surface, the Fab of $\alpha$-P18 increases C9 activation by membrane C5b-8, as monitored by exposure of a complex-dependent C9 neo-epitope. Although $\alpha$-P18 causes little increase in the cytolysis of platelets treated with C5b-9 (as determined from the total release of lactate dehydrogenase of less than 5%), it markedly increases the cell stimulatory responses induced by these complement proteins, including secretion from platelet alpha and dense granules, conformational activation of cell surface GP IIb–IIIa, release of membrane microparticles from the platelet surface, and exposure of new membrane binding sites for components of the prothrombinase enzyme complex. Prior incubation of C5b67 platelets with 100 $\mu$g/ml $\alpha$-P18 (Fab) lowers by approximately 10-fold the half-maximal concentration of C8 required to elicit each of these responses in the presence of excess C9. Incubation with $\alpha$-P18 (Fab) alone does not activate platelets, nor does incubation with this antibody potentiate the stimulatory responses of platelets exposed to other agonists.

As used herein in the compositions and methods for the prolongation of platelet and organ survival and enhancement of therapeutic efficacy or suppression of complement mediated disorders, "C5b-9 inactivator" refers to any CD59 molecule, including the 18 kDa protein on erythrocyte membranes, peptide fragments thereof having C5b-9 inhibitory activity, preferably containing a membrane binding domain, whether isolated from naturally produced materials or recombinantly engineered sequences. The term also includes cells infected or transfected with, and expressing, the gene for CD59 or a biologically functional portion thereof, as well as cells in transgenic animals in which the gene in combination with a promoter such as the murine Kd MHC class I promoter has been stably introduced into an embryo of the animal using a technique such as microinjection. All molecular weights are determined by SDS-PAGE under non-reducing conditions.

These 'studies are described in more detail in the following non-limiting examples. The teachings of the cited references are specifically incorporated by reference herein.

Experimental Procedures

Materials: Human complement proteins C5b6, C7, C8 and C9 were purified and analyzed for functional activity according to methods described by Wiedmer and Sims, *J. Biol. Chem.* 260, 8014–8019 (1985). Human serum deficient in complement protein C8 (C*D) and the human complement proteins C8 and C9 were prepared and assayed according to Sims, P. J. *Biochemistry* 23, 3248–3260 (1984), and Cheng, K., et al., *J. Immunol.* 135, 459–464 (1985). Methotrexate was purchased from Lederle Laboratories (Carolina, Puerto Rico). BCECF/AM was from Molecular Probes (Eugene, Oreg.). N-Glycanase was from Genzyme (Cambridge, Mass.). All other chemicals were of reagent or analytical grade.

Solutions

Hanks' balanced salt solution (HRSS) was purchased from Whittaker M.A. Bioproducts (Walkersville, Md.) and made 1% (w/v) in fatty acid-free bovine serum albumin (Sigma).

Antibodies

Monoclonal antibody against CD59 (1F1) was obtained from Dr. Motowo Tomita (Showa University, Tokyo). Fab fragments of monospecific rabbit antibody against human erythrocyte CD59 were prepared as described by Sims, P. J., Rollins, S. A., and Wiedmer, T. (1989). Rabbit antiserum reactive with CHO membranes was prepared by repeated injection of plasma membranes derived from cultured CHO cells, and the IgG fraction (anti-CHO) was prepared by affinity purification using protein A-Sepharose (Sigma). Rabbit anti-human erythrocyte was purchased from Cappel (Cochranville, Pa.).

Erythrocyte Membrane Protein Inhibitory for C5b-9

The 18 kDa human erythrocyte protein inhibitory for C5b-9 mediated activation and lysis, CD59, was isolated by modification of methods described by Sugita, et al. (1988). Additional purification was obtained by Mono-Q™ FPLC (Pharmacia). When incorporated into erythrocytes, this protein inhibited the hemolytic activity of the purified human C5b-9 proteins, due to inhibition of C9 activation by membrane C5b-8. When subjected to 12% polyacrylamide SDS-PAGE (non-reducing), all of the C5b-9- inhibitory activity of this protein was found to elute from a gel slice corresponding to a single protein band at 18 kDa molecular weight.

In addition to classical protein purification using column chromatography, an example of which is discussed above, polypeptides having inhibitory activity can also be affinity purified using inhibitor specific antibodies. Antibodies, such as α-P18, which bind the C5b-9 inhibitor polypeptide, are immobilized on chromatographic matrix material by techniques well known to those skilled in the art, the material containing the 18 kDa protein passed over the chromatographic matrix, non-binding material removed by washing, then the bound material removed with a higher salt solution or similar technique.

For example, erythrocytes, other blood cells that express the CD59 antigen or functionally active fragment thereof, or non-primate cells transfected or infected with the CD59 gene or fragment thereof so as to synthesize the CD59 or functionally active fragment thereof is then purified from other proteins by conventional methods of ion-exchange chromatography, as described by Sugita, et al., (1988) or Sims, et al., (1989), the teachings of which are incorporated herein, or by absorption to a matrix or immobilized antibody raised against the protein, either in a batch process or chromatographically. The resultant solubilized crude extract is then mixed with matrix immobilized antibody either in a batch process or chromatographically. The immobilized antibodies specifically bind C5b-9 inhibitor polypeptides while the remainder of the crude extract is removed by washing. The purified inhibitor is then eluted and collected.

Alternatively, polypeptides having the ability to inhibit C5b-9 mediated procoagulant responses are produced recombinantly. Nucleic acid sequences encoding CD59 or active fragments thereof, are isolated from a human cDNA library, or, preferably, the clone described herein. For example, human DNA is isolated and digested with restriction enzymes to create fragments of appropriate size and with appropriate cohesive ends to be ligated into any of the known and commercially available expression vectors (e.g. Promega's lambda gt11 vector system). Alternatively, the isolated DNA is sheared and the appropriate linkers are ligated onto the resulting fragments which are then inserted into the expression vector of choice.

Vectors containing human DNA fragments are next transformed into the appropriate bacterial strain, normally a strain of *E. coli* that is included in the expression vector kit, to generate the DNA gene bank or library. Plating out the vector containing bacteria of the library on appropriate media results in expression of the inserted human DNA fragment. The colonies are screened for the presence of DNA encoding and expressing the C5b-9 inhibitory polypeptide using specific antibodies such as α-P18. Positive colonies are isolated and used for the large scale expression of recombinantly produced inhibitory protein.

In this fashion intact inhibitory protein can be made recombinantly as well as modified polypeptides and functional fragments and derivatives thereof. Functional polypeptides possessing the tertiary structure and ability to inhibit C5b-9 can be produced by any of the above discussed method or by other techniques commonly known to those of ordinary skill in the art. These isolated and purified polypeptides can be further mixed with pharmaceutically acceptable carriers to form compositions for use in prolonging cell storage or in treatment of immune disorders or diseases.

The following methods are useful in detecting and quantitating C5b-9 inhibitory activity of CD59 or fragments thereof.

Protein Labeling for fluorescence or radiolabelling

For flow cytometry, all antibodies were conjugated with fluorescein isothiocyanate (FITC). The IgG fraction of affinity-purified goat antibody against murine IgG (Sigma) was labeled with FITC anti-mouse IgG. Dye:protein ratios range from 3 to 6. In all cases, unincorporated label ($^{126}$I or FITC) is removed by gel filtration followed by exhaustive dialysis.

Monoclonal antibody 1F1 was radiolabeled with IODO-GEN™ (Pierce Chemical Co.) to a specific activity of 6221 cpm/ng.

Protein Concentrations

Concentrations of unlabeled proteins are estimated assuming the following extinction coefficients ($E^{1\%}_{280}$): murine IgG (15), C8 (15.1), and C9 (9.6). The concentrations of FITC-labeled proteins are determined by dye binding assay (BioRad), using the respective unlabeled protein as standard. FITC concentration is determined assuming a molar extinction (492 nm) of 68,000.

Phospholipase C Cleavage of CD59

Confluent monolayers of CD59-transfected CHO cells maintained in 1.0 mg/ml methotrexate were released from T-25 tissue culture flasks with Versene/EDTA (Whittaker M.A. Bioproducts). After washing and suspension to $2\times10^6$ cells/ml in HBSS, these cells were exposed to 1.0 unit/ml phosphatidylinositol-specific phospholipase C (ICN Biochemicals, Indianapolis, Ind.) or enzyme diluent buffer as a control. After incubation for 1 h at 37° C., 25 μl of each cell suspension was added to tubes containing 25 μl of monoclonal antibody 1F1 (final concentration 10 μg 1F1/ml in HBSS). After 30 min of incubation at 4° C., 10 μl of FITC anti-mouse IgG was added (final concentration, 87 μg IgG/ml), and cells were incubated for an additional 15 min at 23° C. Surface CD59 was quantitated by specific binding of monoclonal antibody 1F1, measured by a FACSCAN (Becton, Dickinson & Co.) flow cytometer with the FL1 fluorescence channel (520 nm) set at logarithmic gain.

Western Blotting

Purified human erythrocyte CD59 (1 μg) and the antigen from CD59 transfected CHO cells were denatured (3 min, 100° C.) in 2% SDS under nonreducing conditions and electrophoresed in a 15% homogenous gel using a Laemmli, U. K. *Nature* 227, 680–685 (1970), buffer system. Following transfer to nitrocellulose, immunoblotting was performed by overnight incubation at 23° C. with either monoclonal anti-CD59 (10 μg/ml) or rabbit anti-CD59 (10 μg/ml) in TBS (150 mM NaCl, 50 mM Tris, pH 7.4) with 1% bovine serum albumin. Blots were developed with a 1:1000 dilution of the appropriate alkaline phosphatase-conjugated anti-rabbit or anti-mouse IgG (Sigma).

EXAMPLE 1

Transfection and Expression of CD59 CDNA in CHO Cells

The EcoRI fragment that encodes the CD59 protein, described by Philbrick, W. M., et al., *Eur. J. Immunol.* 20, 87–92 (1990, was subcloned into the EcoRI site in the μFRSV expression vector, reported by Slanetz, A. E., and Bothwell, A. L. M. *Eur. J. Immunol.* 21, 179–183 (1991).

The amino acid sequence for the protein encoded by this insert is: L Q C Y N C P N P T A D C K T A V N C S S D S D A C L I T K A G L Q V Y N K C W K F E H C N F N D V T T R L R E N E L T Y Y C C K K D L C N F N E Q L E N G G T S L S E K T V L L L V T P F L A A A W S L H P.

The cDNA sequence encoding the CD59 protein is: CTGCAGTGCTACAACTGTCCTAACCCAACTGCT (SEQ. ID NO.1) GACTGCAAAACAGCCGTCAATTG-TTCATCTGATTTTGATGCGTGTCTCATTACCAAAG-CTGGGTTACAAGTGTATAACAAGTGTTGGAAGTT-TGAGCATTGCAATTTCAACGACGTCACAACCCGC-TTGAGGGAAAATGAGCTAACGTACTACTGCTGCA-AGAAGGACCTGTGTAACTTTAACGAACAGCTTGA-AAATGGTGGGACATCCTTATCAGAGAAAACAGT-TCTTCTGCTGGTGACTCCATTTCTGGCAGCAGCC-TGGAGCCTTCATCCCTAAGTC(SEQ. ID NO.2).

The FRSV.CD59 vector was linearized with SalI (20 μg) and introduced into 10⁷ CHO cells by electroporation (2 kV, 25 microfarads). The cells were plated in minimum Eagle's medium (GIBCO) containing 10 mg/ml adenosine, thymidine, and deoxyadenosine and maintained for 1 to 2 days. The medium was then replaced with minimum Eagle's medium lacking deoxynucleosides but containing 0.09 μg/ml methotrexate and 10% dialyzed fetal calf serum (GIBCO). After 2 to 3 weeks, individual clones were isolated, expanded, and selected at increasing levels of methotrexate.

The resulting transfectants were subcloned and selected for growth in medium that is supplemented with methotrexate and then amplified by continuous culture in incremental concentrations of methotrexate ranging up to 1 mg/ml, as shown in FIG. 1.

Immunoblotting of CD59 expressed by transfected CHO cells and human erythrocytes was performed. Immunoblots were developed with monoclonal antibody 1F1 (10 μg/ml) and rabbit anti-CD59 IgG (10 μg/ml). The transfected CHO cell-derived protein had a greater molecular weight than the native molecule.

Based on the specific binding of radiolabeled monoclonal antibody against this antigen, cell-surface CD59 was increased from 0 (in nontransfected CHO controls) to approximately $4.2 \times 10^6$ molecules/cell (for those CD59 transfectants maintained in 1 mg/ml methotrexate).

Quantitation of Cell-surface CD59 Antigen

The specific binding of $^{125}$I-labeled 1F1 was utilized to quantitate the level of CD59 antigen expressed by CD59-transfected CHO cells. The CHO cells (CD59 transfectants and controls) were grown to confluence in 48-wall tissue culture plates, washed in HBSS, and then fixed with 1% paraformaldehyde (10 min, 23° C.). After washing to remove fixative, the cells were incubated with a saturating concentration of antibodies, 10 μg/ml $^{125}$I -1F1, for 30 min at 23° C. The cells were then washed six times in ice-cold HBSS, and cell-associated antibody was eluted with 4% sodium dodecylsulfate (SDS). Radioactivity was measured by photon counting and corrected for nonspecific binding, measured in the presence of a 20-fold excess of unlabeled antibody. Data for CD59 transfectants was expressed as increase in surface antigen relative to nontransfected CHO cell controls.

Subcloning of a CDNA clone for human CD59 into the eukaryotic expression vector PFRSV and transfecting into CHO cells via electroporation demonstrates that CD59 can be expressed in cells not normally expressing CD59 or HRF and confer protection from complement mediated lysis. Although PFRSV was chosen to incrementally amplify the DNA flanking the dihydrofolate reductase locus in a methotrexate concentration-dependent manner, other vectors could also be used such as pFRSV-SLα or other retroviral vectors.

The vector PFRSV has been used successfully to increase expression after gene amplification by selection in methotrexate containing medium. The plasmid vector pFRSV-SRα has a much stronger promoter driving expression of the introduced cDNA. The SalT-EcoRI fragment (800 bp) from pcDL-SRα296 (Takebe, et al., *Molec. Cell Biol.* 8:466–472 (1988)) was inserted into the HindIII-EcoRI site of pFRSV, described by Slanetz and Bothwell, (1991). This plasmid expresses much higher basal levels of CD59 and other inserted cDNAs than the pFRSV vector.

Expression in mammalian cells, especially endothelial cells may also be accomplished by infection utilizing retrovirus vectors. This method is more gentle and efficient than electroporation as a means of introducing the DNA into cells. Retroviruses that bear different drug resistance markers for selection provides a means for introducing multiple cDNAs for expression in endothelial cells. Retroviruses currently under development for this purpose include the use of the neo, hygrogycin and histidinol as selectable markers. All of these resistance genes are available on BamIII fragments and can be easily inserted into retroviral vectors to alter the resistance of a given vector. The DHFR gene is also available in retrovirus vectors. Retroviruses that express CD59 driven by the SRα promoter or the retroviral LTR (long terminal repeat) promoter can be utilized.

The use of retroviruses that bear distinct drug resistance markers will facilitate the co-expression of CD59 with either DAF(CD55) or MCP(CD46). Co-expression with CD59 may be more effective than CD59 alone in minimizing endothelial cell activation. Although desirable, it is not essential for the retrovirus vector to bear a drug resistance marker. Retroviruses may be developed that express both CD59 and CD55 or CD46 from a single virus. It is also possible to utilize vectors bearing different drug markers for expression of all three complement regulatory proteins CD59, CD55 and CD46.

EXAMPLE 2

Molecular weight comparison of recombinant, natural, and de-glycosylated CD59.

Membrane proteins from CD59-transfected CHO cells (CD59 expression amplified by growth in 1 mg/ml methotrexate) were extracted with 2% Triton X100, 20 mM Tris, 10 mM EDTA, 50 mM benzamidine, 200 mM N-ethylmaleimide, 1 mM phenylmethylsulfonyl fluoride, pH 7.4. After removal of insoluble material by centrifugation at 11,000×g, 5 min, the detergent extracts were diluted 10-fold, and CD59 antigen was purified by immunoaffinity chromatography using antibody immobilized on Affi-Gel 10 (Bio-Rad). Antigen was eluted with 1 M glycine, 0.2% Triton X-100, 10 mM EDTA, 56 mM benzamidine, 200 mM N-ethylmaleimide, 1 mM phenylmethylsulfonyl fluoride, pH 3.0; dialyzed against 200 mM sodium phosphate, 10 mM EDTA, 50 mM benzamidine, 200 mM N-ethylmaleimide, 1 mM phenylmethylsulfonyl fluoride, pH 8.6; and concentrated to 200 µg/ml. After denaturation under reducing conditions (0.5% SDS, 100 mM P-mercapoethanol; 100° C., 3 min), immunoaffinity-purified CD59 was incubated (37° C., 24 h) with 30 units/ml of N-glycanase in the presence of 10 mM 1,10-phenanthroline and then analyzed by silver staining after 8–25% SDS-PAGE (PHAST System, Pharmacia LKB Biotechnology Inc.).

Figure 2:
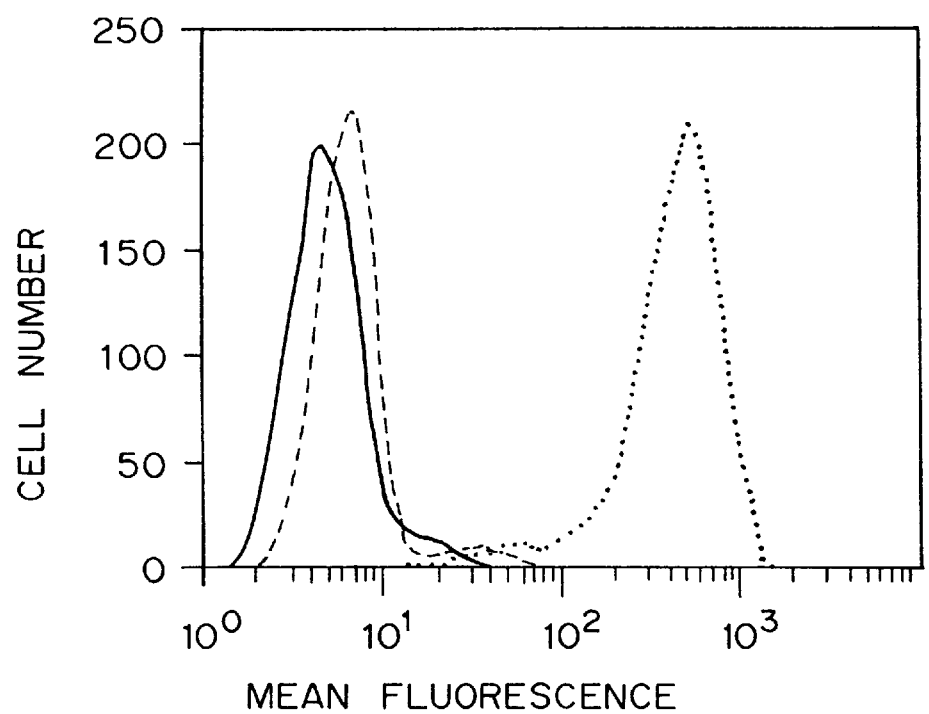
FIG. 2 is a graph of the removal of cell-surface CD59 by phosphatidylinositol-specific phospholipase C (PIPLC), plotting cell number versus mean fluorescence. CD59-transfected CHO cells amplified by growth in 1 mg/ml methotrexate were suspended at $2 \times 10^6$/ml in HBSS and incubated for 1 h at 37° C. with either 0 ( . . . ) or 1 (- - -) unit/ml phosphatidylinositol-specific phospholipase C. Cell-surface CD59 was then measured by flow cytometry using monoclonal antibody 1F1 (10 μg/ml), which was detected with FITC anti-mouse IgG (67 μg/ml). Histograms denote mean fluorescence per cell on logarithmic scales. Also shown is background cell fluorescence measured in the absence of 1F1 (- - -)

Recombinant CD59 expressed on the surface of these cells was susceptible to removal by phosphatidylinositol-specific phospholipase C digestion, consistent with its attachment to the membrane via a glycolipid anchor, as shown in FIG. 2. By Western blotting, CD59 expressed by the transfected CHO cells exhibited a distinctly slower migration on SDS-PAGE (apparent molecular mass of 21–24 kDa) than CD59 present in human erythrocytes (apparent molecular mass of 18–21 kDa). After digestion with N-glycanase to remove asparagine-linked carbohydrate, recombinant CD59 isolated from CHO transfectants and CD59 isolated from human erythrocytes co-migrated, with apparent molecular masses of 12–14 kDa by SDS-PAGE.

EXAMPLE 3

Protection of CD59-transfected CHO Cells from Pore-forming Activity of Human C5b-9

The functional activity of recombinant CD59 expressed in the transfected CHO cells was evaluated by assaying complement-mediated dye release using the intracellular fluorescent dye indicator BCECF/AM. By taking advantage of the capacity to incrementally amplify gene expression by growth in various concentrations of methotrexate, as shown in FIG. 1, the inter-relationship of the CD59 antigen level to C5b-9 inhibitory activity was evaluated.

After stable expression at each methotrexate concentration was achieved, the CD59 transfected cells were tested for sensitivity of human serum complement using a BCECF/µM dye release assay. After incubation with BCECF/AM (15 µM) and washing, confluent monolayers were incubated with 5 mg/ml rabbit anti-CHO IgG and 25% C8D to deposit C5b-67 on the plasma membrane. Then, human serum containing 10 mM EDTA was added as the source of C8 and C9. Dye release into the supernatant was determined after 15 min at 37° C., with correction for nonspecific release observed for matched controls, omitting incubation in C8D.

Figure 3:
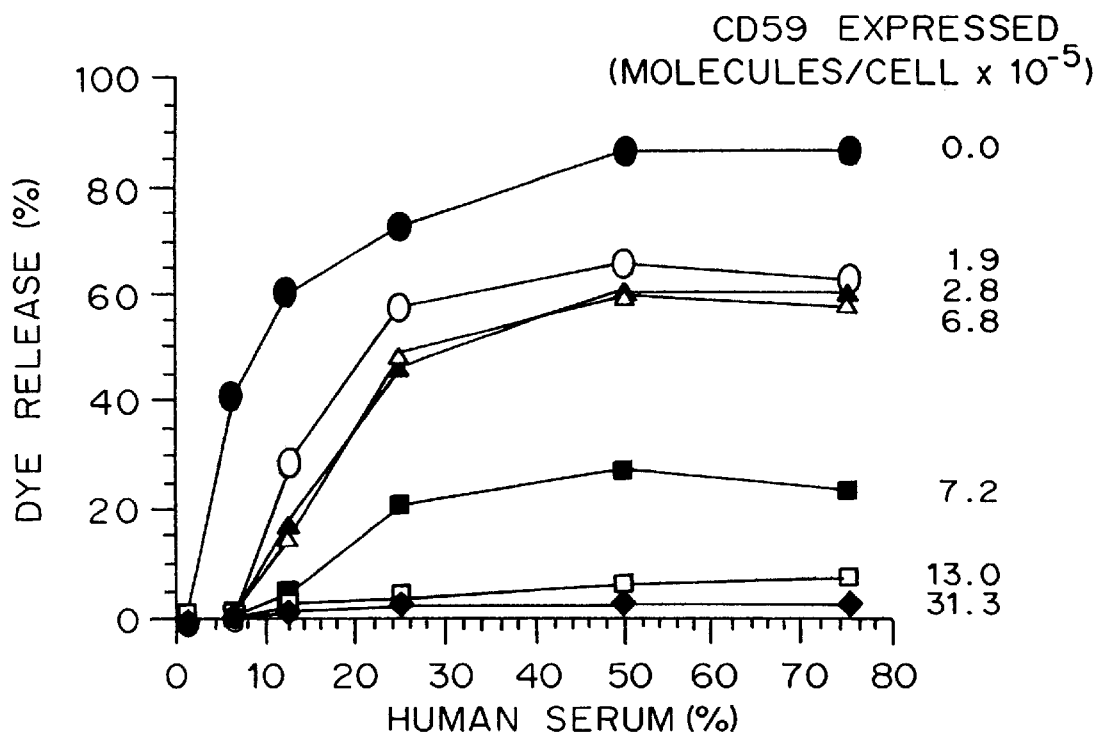
FIG. 3 is a graph showing protection of CD59-transfected CHO cells from human serum complement, dye release (%) versus human serum (%). CD59-transfected CHO cells were inducted to express various amounts of CD59 antigen by growth in methotrexate-containing media, molecules CD59 expressed/cell$\times 10^{-5}$: 0.0 (dark circles), 1.9 (open circles), 2.8 (dark diamonds), 6.8 (open triangles), 7.2 (dark squares), 13.0 (open squares), and 31.3 (dark diamonds).

As shown in FIG. 3, increased amplification of the expression of CD59 resulted in a marked decrease in the sensitivity of the transfected CHO cells to dye release induced by immune activation of human serum complement. For cells grown in 200 µg/ml methotrexate (representing amplification of cell-surface expression to approximately 1.2×10$^6$ molecules of CD59/cell), no complement-mediated dye release was observed, even at the highest concentrations of serum tested (75%).

To demonstrate complement inhibitory activity, CD59 expression of transfected CHO cells was amplified by growth in 50 µg/ml methotrexate: the cells were loaded with dye by incubation in BcECF/AM; and C5b-67 was deposited as described for FIG. 3. After washing, the cells were incubated (4° C., 30 min) with either 0 mg/ml or 0.5 mg/ml functionally inhibitory antibody (Fab fragments) to CD59. Unbound antibody was removed; C8 (1 µg/ml) and varying amounts of C9) were added; and dye release was measured after 15 min at 37° C.

Figure 4:
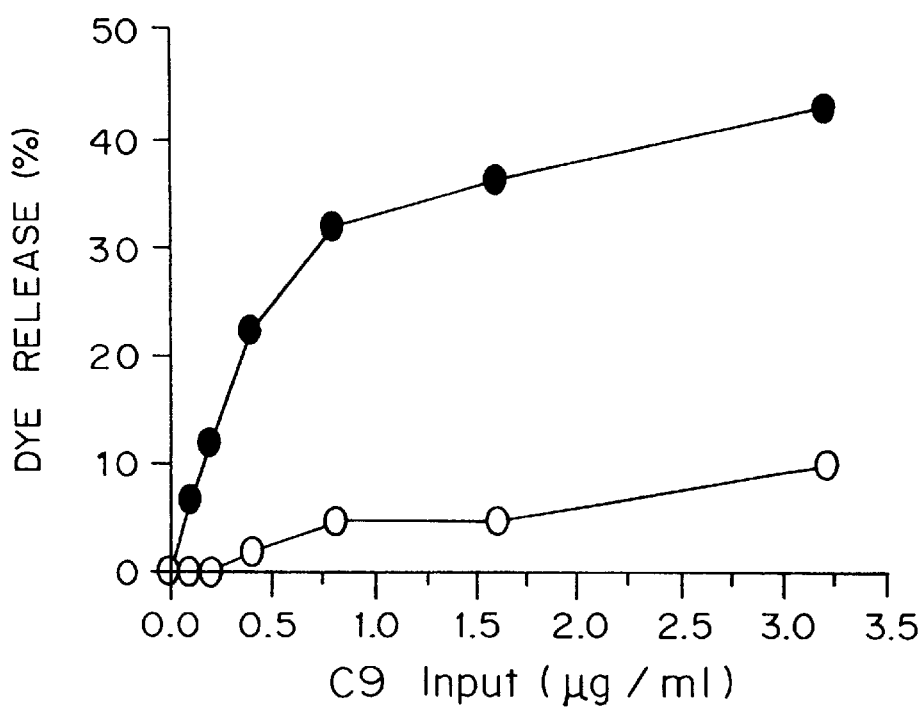
FIG. 4 is a graph of neutralization of C5b-9 inhibitory activity expressed by CD59-transfected CHO cells by antibody to CD59, dye release (%) versus C9 input (μg/ml). The cells were incubated (4° C., 30 min) with either 0 mg/ml (open symbols) or 0.5 mg/ml (closed symbols) functionally inhibitory antibody (Fab fragments) to CD59. Unbound antibody was removed; C8 (1 μg/ml) and varying amounts of C9 were added; and dye release was measured after 15 min at 37° C. Dye release at each C9 input was determined with correction for nonspecific leakage and is expressed as the percentage of total determined for detergent-lysed cells.

As shown in FIG. 4, the resistance to complement-mediated membrane damage observed for CD59-expressing CHO cells reflected inhibition of C9-dependent activation of the complement pore, and this inhibition was reversed by prior incubation of the cells with Fab fragments of a functionally blocking antibody directed against CD59 antigen. These data confirm that the protection against human serum complement observed for CD59 transfectants is related to the expression of cell-surface CD59 and is not due to other changes in these cells that might be induced by long-term culture in methotrexate.

EXAMPLE 4

Human selectivity of Complement Inhibitory Function Expressed by CD59-transfected CHO Cells.

CD59-transfected CHO cells are selectively protected from the effects of the human C5b-9 proteins in a manner analogous to the species-selective resistance to lysis observed for human erythrocytes and for membranes reconstituted with purified CD59 antigen from human erythrocytes. In these studies, anti-CHO IgG and human C8D were used to deposit the human C5b-67 complex on the CHO cell plasma membrane, before incubation in either human or guinea pig serum containing EDTA, as the source of the C8 and C9 components of the C5b-9 complex.

CD59 expression by transfected CHO cells was amplified by growth at various methotrexate concentrations; the confluent monolayers were loaded with BCECF/AM; and human C5b-67 was deposited as described for FIG. 4. After washing, the C5b67 cells were made C5b-9 by incubation (15 min, 37° C.) with either 10% (v/v) human serum (closed symbols) or 10% v/v) guinea pig serum (open symbols) in the presence of 10 mM EDTA.

Figure 5:
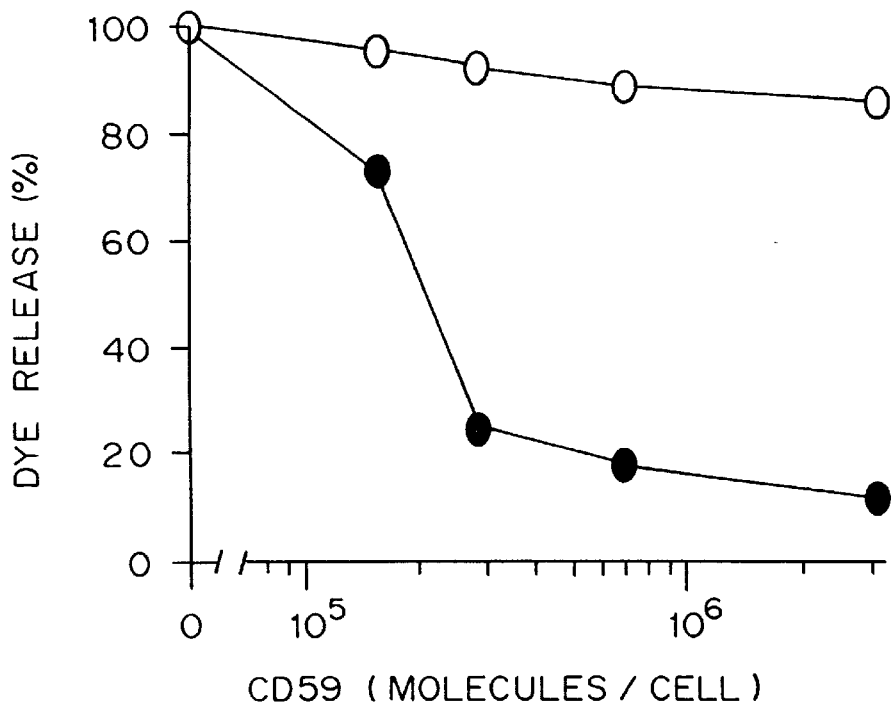
FIG. 5 is a graph of CD59 expressed by transfected CHO cells inhibiting human (but not guinea pig) C8 and C9, dye release (%) versus CD59 (molecules/cell). C5b-9-specific dye release was determined with correction for nonspecific dye leakage and is expressed as relative to the dye release from C5b-9-treated CHO controls (nontransfected).

As illustrated by FIG. 5, CD59 expressed by transfected CHO cells protected these cells from pore formation by human C5b-9, but not when the C8 and C9 components of this complex were replaced by the guinea pig proteins.

Human C5b-67 was deposited on K562 cells by successive incubation with anti-human erythrocyte antiserum (1.5t (v/v, containing 10 mM EDTA) and 60% (v/v) human C8-depleted serum (diluted in HBSS). After loading with BCECF/AM cells were incubated (4° C., 30 min) with either 0 mg/ml or 1 mg/ml of functionally- blocking antibody to CD59. After removal of unbound antibody, the cells were made C5b-9 by incubation in either human (circles) or guinea pig (triangles) serum containing 10 mM EDTA.

Figure 6:
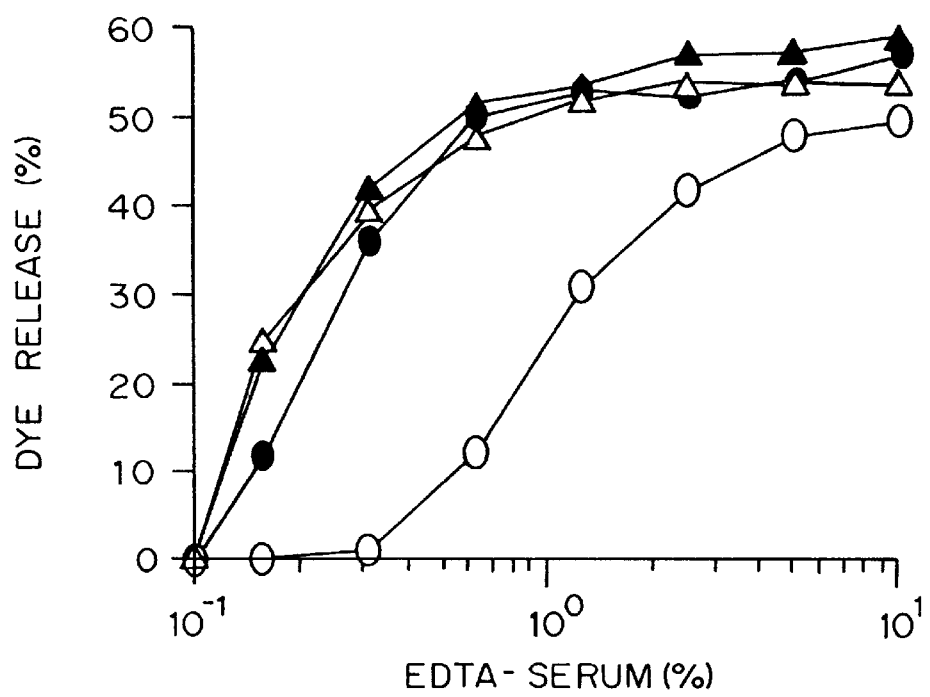
FIG. 6 is a graph of CD59 expression by K562 cells, dye release (%) versus EDTA-serum (%). After loading with BCECF/AM, cells were incubated (4° C., 30 min) with either 0 mg/ml (open symbols) or 1 mg/ml (closed symbols) of functionally- blocking antibody to CD59. After removal of unbound antibody, the cells were made C5b-9 by incubation in either human (circles) or guinea pig (triangles) serum containing 10 mM EDTA. Dye release was determined after 15 min at 37° C. with correction for nonspecific leakage and are expressed as percent of total.

As shown in FIG. 6, this capacity to restrict the pore-forming activity arising upon incorporation of human (but not guinea pig) C8 and C9 into C5b-9 was also observed for CD59 constitutively expressed on the surface of human K562 cells, the cell line from which the cDNA for CD59 used in these studies was originally derived.

EXAMPLE 5

Administration of, or Expression of, CD59 in cells to protect the cells from complement-mediated activation and lysis It is apparent from the data in U.S. Pat. No. 5,135,916 and the preceding examples that inactivation of functional C5b-9 inhibitor or a reduction in the platelet or endothelial cell membrane concentration of C5b-9 inhibitor molecules results in increased platelet or endothelial cell activation. Conversely, administration or expression of this inhibitor, or a polypeptide representing its functional domain and possessing C5b-9 inhibitory activity produced from the isolated naturally produced inhibitor or from genetically engineered cells expressing (or more preferably, secreting) inhibitor, to block platelet or endothelial cell activation in a patient in need of such treatment, would thereby protect the patient from C5b-9 mediated procoagulant and prothrombotic responses.

Platelets obtained from patients with the acquired stem cell disorder Paroxysmal Nocturnal Hemoglobinuria (PNH) have been shown to exhibit abnormal sensitivity to fluid phase complement activation, as characterized by an unusually high risk of venous thrombosis. This same finding is equally applicable to other types of complement mediated disorders, particularly in view of the discovery that the inhibitor is also found on the surface of endothelial cells. As a result, administration of the inhibitor protein, whether purified from cells or expressed from cells engineered using recombinant techniques, or portions of the peptide having the same measurable activity, can be administered to these patients to alleviate the severity of the disorder.

Treatment of patients with immune disorders and diseases such as immunovasculitis, rheumatoid arthritis, scleroderma, disseminated intravascular coagulation, lupus, paroxysmal nocturnal hemoglobinuria, thrombotic thrombolytic purpura, vascular occlusion, reocclusion after surgery, coronary thrombosis, and myocardial infarction, is accomplished by administering an effective amount of a composition containing a C5b-9 inactivator as defined above such that procoagulant processes are suppressed. In the case of transfused blood cells, progenitor hematopoietic stem cells derived from or contained in bone marrow used for transplantation, or transplanted organs or tissue, the purified membrane inhibitor of C5b-9, or the functionally equivalent polypeptide or antibody, is first coated on the cell surface or the gene introduced into the precursor cells before transplantation or transfusion into the recipient. The precursor cells could be derived from the same species of origin as the recipient or from transgenic animals of a different species wherein the gene for CD59 for the recipient species is introduced into an embryo using techniques known to those skilled in the art such as microinjection. The amount of composition that must be administered to a patient in need of such treatment will vary depending on the particular disorder or disease and the severity of affliction. Treatment dosages will also vary with the individual patient depending upon response to treatment, genetic variability, and effect of co-administered drugs. In general, however, the compositions disclosed herein are administered intravenously at a dosage of approximately nanograms of inhibitory protein or peptide per milliliter, or gene expression used to effect surface expression of at least $1 \times 10^3$ molecules/cell or 1 molecule CD59/$\mu m^2$. Treatment can take the form of a single administration of the composition or can be administered periodically or continuously over an extended period of time, as required. For treatment of immune disorder or disease, the C5b-9 inactivator is administered intravenously in a pharmaceutically acceptable carrier such as saline or a physiologically acceptable buffer. In some cases, it may be advantageous to administer CD59 in combination with genetically engineered cells to maximize effectiveness.

Isolated, functionally active polypeptides having the appropriate tertiary structure to inhibit C5b-9 have utility for increasing the hemostatic efficacy and extending the in vitro storage time of blood and platelet preparations. There exists a great need for prolonging the half-life, and therapeutic efficacy of platelets stored in vitro. Platelet-containing solutions, particularly platelet-rich plasma (PRP), are in tremendous demand medically for transfusions. The current shelf life of platelet preparations is approximately 72 hours. An increase in the useful lifetime of such preparations represents a significant advancement in the state of the art and answers a pressing human and medical need.

In the case of human organs and tissue for transplantation, the C5b-9 inactivators would be added to the perfusate or storage medium to protect the vascular lining cells from ongoing complement activation during in vitro storage. Additionally, by coating these endothelial cells with a membrane-anchored C5b-9 inactivator or inserting into the cells the gene for expressing the C5b-9 inactivator, the organ or tissue would be protected from the cytolytic and thrombotic effects arising from complement activation initiated upon transplantation, thereby circumventing complement mediated acute rejection. The gene for CD59 is ligated to a vector suitable for high level expression of the gene in the target mammalian cells. This plasmid is introduced into the cells to be transfused or tissue to be transplanted by the technique of transfection or infection at 12 to 24 hours prior to infusion or transplantation. In the case of vascularized organs to be transplanted, transfection of the plasmid of the vascular endothelial cells lining the blood vessels is performed. It may be preferable in some cases to transfect the gene encoding CD59 of the same species as the cells to be protected so that the cells overexpress CD59 on their surface and are therefore made more resistant to complement mediated lysis or activation. For example, the gene for human CD59 may be introduced into human endothelial cells expressing CD59 to increase their resistance to complement mediated lysis or activation.

In the preferred embodiment, the C5b-9 inactivator is administered in combination with anticoagulant, such as ACD, CPD, heparin, or oxalate, such that the concentration in the platelets or PRP is approximately nanograms inactivator/ml, or expressed at a concentration of at least $1 \times 10^3$ inhibitor/ml. Similarly, for organ storage, the C5b-9 inactivator is in combination with perfusate or storage solutions, or culture medium, such that the concentration is approximately nanograms inactivator/ml.

It is apparent from the foregoing discussion that addition of polypeptides which act to inhibit the activity of C5b-9 towards human platelets and endothelium would reduce the incidence of C5b-9 mediated procoagulant and prothrombotic responses. Release of platelet granule enzymes and factors result in clotting of platelets and general deterioration of the platelet preparation, limiting the shelf life of such preparations. Thus, the addition of the disclosed compositions containing C5b-9 inhibitory polypeptides to platelet preparations will suppress the spontaneous initiation of a procoagulant state and increase the usable life of such preparations.

Compositions useful for extending the shelf life of platelet preparations stored in vitro contain C5b-9 inhibitor in an amount sufficient to inhibit C5b-9 mediated platelet activation. Generally, these compositions will be added to platelet preparations, such as platelet-rich plasma, such that the final concentration of inhibitory polypeptide in the preparation is in the range of greater than 2 Ki (Ki=concentration of half maximal inhibition) of the inactivator in the solution. For CD59 and other polypeptides which incorporate a membrane binding domain, the therapeutically effective dosage will be less than 1 μg inactivator/ml, or at least 1×10³ molecules inactivator/platelet or other cell. Useful compositions may also contain additional anticoagulant agents such as oxalate, citrate, and heparin. The C5b-9 inhibitor containing compositions can be added to whole blood as it is collected or to platelet preparations after processing of the blood into isolated platelet concentrates.

By increasing the surface concentration of these complement-inhibitors in the plasma membrane by increasing the level of transcript mRNA for the protein, the cells are protected from activated complement C5b-9 after infusion or tissue/organ transplantation.

The effective potency of CD59 and other inhibitors of the C5b-9 complex depends on the number of C5b-9 complexes generated per unit area of plasma membrane. Therefore, the inhibitory effect of CD59 on the cytolytic and cell-stimulatory activity of C5b-9 can be overcome by increasing the input of the activated complement components that are required for assembly of the C5b-9 complex. The protective effects of CD59 can be augmented by providing CD59 in conjunction with CD46 and/or CD55. As detailed below, in this formulation, CD59 is expressed in conjunction with CD46 and/or CD55 by transfection or infection with a vector containing the gene for each protein. The co-expression of these genes will serve to limit the amount of C5b-9 that can be generated at the cell surface (through the inhibitory effects of CD46 and/or CD55 on the conversion of C5 to C5b by the complement enzymes) and to protect from the cytolytic and cell-stimulatory effects of the residual C5b-9 that is formed through conversion of C5 to C5b by plasmin and other enzymes that are not inhibited by the action of CD46 and/or CD55.

Modifications and variations of the present invention will become obvious to one skilled in the art in view of the description. These modifications and variation are intended to fall within the scope of the appended claims.

We claim:

1. A method for protection of platelets or endothelial cells from complement activation and lysis by inhibition of complement proteins comprising:

providing a vector comprising a gene encoding CD59 having a molecular weight of 18-24 kDa as determined by SDS-PAGE under non-reducing conditions, wherein said CD59 is of the same species as the complement proteins to be inhibited, introducing said vector into a host cell system for expression of the gene, culturing the host cells under conditions wherein the gene is expressed, isolating said CD59, and combining said CD59 with the platelets or endothelial cells to be protected from activation or lysis.

2. The method of claim 1 wherein the host cells are non-mammalian cells.

3. The method of claim 1 wherein the CD59 is soluble.

4. The method of claim 1 wherein the CD59 is not glycosylated.

5. The method of claim 1 wherein the glycosylation of the CD59 has been altered.

6. A method for the protection of mammalian platelets or mammalian endothelial cells from complement activation and lysis by inhibition of complement proteins comprising:

providing a vector comprising a gene encoding CD59 having a molecular weight of 18–24 kDa as determined by SDS-PAGE under non-reducing conditions, wherein said CD59 is of the same species as the complement proteins to be inhibited, and introducing said vector into the platelets or endothelial cells to be protected from activation or lysis, wherein said gene is expressed on the surface said cells.

7. The method of claim 6 wherein the platelets or endothelial cells have on their surface greater than or equal to $10^3$ CD59 molecules/cell or greater than or equal to 1 molecule of CD59 antigen/$\mu m^2$ of plasma membrane surface.

8. The method of claim 6 wherein the gene encoding CD59 is transfected into the mammalian platelet or endothelial cells using a retroviral vector.

9. The method of claim 6 wherein the platelets or endothelial cells are human and are transfected with the vector comprising the gene encoding CD59, wherein CD59 is overexpressed on the surface of the transfected cells.

10. The method of claim 6 wherein the CD59 is expressed from a gene having the sequence consisting essentially of the sequence set forth in SEQ. ID No.2.

11. The method of claim 1 or 6 wherein the protein sequence of the CD59 consists essentially of the sequence set forth in SEQ ID No.1.

12. The method of claim 1 or 6 wherein the CD59 protein comprises a portion of the sequence set forth in SEQ ID No. 1, wherein said protein inhibits C5b-9 mediated cell lysis.

13. A method for the protection of platelets or hematopoietic progenitor cells from complement activation and lysis by inhibition of complement proteins comprising:

providing a vector comprising a gene encoding CD59 having a molecular weight of 18–24 kDa as determined by SDS-PAGE under non-reducing conditions, wherein said CD59 is of the same species as the complement proteins to be inhibited, introducing said vector into host cells selected from the group consisting of hematopoietic progenitor cells and hematopoietic progenitor progeny, and culturing said host cells under conditions wherein the gene is expressed on the surface of the host cells.

14. The method of claim 1, 6 or 13 further comprising providing molecules selected from the group consisting of CD46 and CD55.

15. The method of claim 14 wherein the molecules are in solution.

* * * * *